(12) United States Patent
Murthy

(10) Patent No.: US 7,282,487 B2
(45) Date of Patent: *Oct. 16, 2007

(54) METHOD FOR TREATING BACTERIAL INFECTIONS IN HORSES OR PIGS WITH TILMICOSIN

(75) Inventor: Yerramilli V. S. N. Murthy, Apex, NC (US)

(73) Assignee: Idexx Laboratories, Westbrook, ME (US)

( * ) Notice: Subject to any disclaimer, the term of this patent is extended or adjusted under 35 U.S.C. 154(b) by 257 days.

This patent is subject to a terminal disclaimer.

(21) Appl. No.: 10/974,877

(22) Filed: Oct. 28, 2004

(65) Prior Publication Data

US 2006/0094669 A1    May 4, 2006

(51) Int. Cl.
*A61K 31/70* (2006.01)
(52) U.S. Cl. .................................. 514/30; 424/400
(58) Field of Classification Search ................ 424/400; 514/37, 39, 152, 30
See application file for complete search history.

(56) References Cited

U.S. PATENT DOCUMENTS

| | | | |
|---|---|---|---|
| 4,298,375 A | 11/1981 | Howe et al. | 71/90 |
| 4,539,401 A | 9/1985 | Hayakawa et al. | 544/101 |
| 4,820,695 A | 4/1989 | Debono et al. | 514/30 |
| 5,574,020 A | 11/1996 | Klink et al. | 514/30 |
| 5,723,447 A | 3/1998 | Macy et al. | 514/29 |
| 5,747,058 A | 5/1998 | Tipton et al. | 424/423 |
| 5,958,888 A | 9/1999 | Macy et al. | 514/29 |
| 6,034,070 A | 3/2000 | Armbruster | 514/30 |
| 6,074,657 A | 6/2000 | Brown | 424/423 |
| 6,110,905 A | 8/2000 | Patterson et al. | 514/152 |
| 6,239,112 B1 | 5/2001 | Macy et al. | 514/29 |
| 6,310,053 B1 | 10/2001 | Patterson et al. | 514/152 |
| 6,328,961 B1 | 12/2001 | Cutrone et al. | 424/115 |
| 6,403,057 B1 | 6/2002 | Schneider et al. | 424/9.52 |
| 6,504,005 B1 | 1/2003 | Fridkin et al. | 530/303 |
| 6,670,278 B2 | 12/2003 | Li et al. | 438/710 |
| 6,887,487 B2 * | 5/2005 | Murthy et al. | 424/400 |
| 6,946,137 B2 * | 9/2005 | Murthy et al. | 424/400 |
| 7,033,599 B2 * | 4/2006 | Murthy et al. | 424/400 |
| 2003/0130211 A1 | 7/2003 | Murthy et al. | 514/36 |
| 2004/0023899 A1 | 2/2004 | Murthy et al. | 514/37 |

OTHER PUBLICATIONS

Jordan, W. H. et al., "A Review of the Toxicology of the Antibiotic MICOTIL 300", *Vet. Hum. Toxicol.*, 35 (2), pp. 151-157, Apr. 1993.
Main, B. W. et al., "Cardiovascular Effects of the Macrolide Antibiotic Tilmicosin, Administered Alone or in Combination with Propranolol or Dobutamine, in Conscious Unrestrained Dogs", *J. vet. Pharmacol. Therap.*, 19, pp. 225-232, 1996.

* cited by examiner

*Primary Examiner*—Elli Peselev
(74) *Attorney, Agent, or Firm*—Kenyon & Kenyon LLP

(57) ABSTRACT

The invention relates to methods of treating a bacterial infection in a horse or a pig. The method involves administering to the horse or pig a composition comprising (i) a salt made from tilmicosin and a lipophilic acid and (ii) a pharmaceutically acceptable solvent combined together to form an injectable composition that precipitates when injected into water.

25 Claims, 6 Drawing Sheets

METHOD FOR TREATING BACTERIAL INFECTIONS IN HORSES OR PIGS WITH TILMICOSIN

CROSS REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The present invention relates to methods of treating a bacterial infection in a horse or a pig comprising administering to the horse or pig a composition comprising (i) a salt made from tilmicosin and a lipophilic acid and (ii) a pharmaceutically acceptable solvent combined together to form an injectable composition that precipitates when injected into water.

BACKGROUND OF THE INVENTION

The following discussion of the background of the invention is merely provided to aid the reader in understanding the invention and is not admitted to describe or constitute prior art to the present invention.

It is often desirable to extend the release time of an injected drug to increase its duration of action or to reduce its toxic effects. Formulations that are readily soluble in the body are usually absorbed rapidly and provide a sudden burst of the pharmacologically active product as opposed to a more desirable and gradual release of the pharmacologically active product. Although a variety of attempts have been made to provide controlled and extended release of pharmacologically active products they have not succeeded in overcoming all of the problems associated the technology, such as achieving an extended release time, maximum stability and efficacy, reduced toxicity, maximum reproducibility in preparation, and the elimination of unwanted physical, biochemical, or toxicological effects introduced by undesirable matrix materials.

Tilmicosin is an antibiotic in the macrolide class with the following structure:

Tilmicosin is effective against a broad range of bacteria, and is used for the treatment of respiratory diseases in cattle. The free form is moderately soluble in aqueous solutions, while the chloride and phosphate salts are highly soluble. At elevated levels, however, tilmicosin is cardiotoxic and its use in sensitive species such as cats, goats, pigs, and horses has been almost entirely avoided due to safety reasons. The commercial product, Micotil® (Eli Lilly & Co., Indianapolis, Ind.), is a solution of the di-phosphate salt and is described in U.S. Pat. No. 5,574,020. This formulation is effective in cattle, but the formulation rapidly releases the antibiotic and, therefor, results in toxicity in many species, including horses, pigs, dogs, and cats.

United States published patent application no. U.S. 2004/0023899 A1 discloses pharmaceutical compositions comprising the salt of a pharmacologically active compound with a lipophilic counterion and a pharmaceutically acceptable water soluble solvent combined together to form an injectable composition. The compositions can be used to extend the release time of the pharmacologically active compound when the composition is administered to an animal.

SUMMARY OF THE INVENTION

The present invention provides methods of treating a bacterial infection in a horse or pig. The method involves administering to the horse or pig a composition comprising (i) a salt made from tilmicosin and a lipophilic acid and (ii) a pharmaceutically acceptable solvent combined together to form an injectable composition that precipitates when injected into water.

When injected into a mammal, at least a portion of the composition precipitates and releases the tilmicosin over time. The methods of the invention extend the release of tilmicosin and provide a controlled dose of tilmicosin to the treated horse or pig. The present invention enables one to administer tilmicosin in a controlled manner to provide a therapeutically effective amount of tilmicosin to the horse or pig for periods of up to 15 days or even longer. The methods of the present invention enable one to administer tilmicosin to the treated horse or pig to provide a pharmaceutically effective amount of tilmicosin for 4-15 days, including any specific number of days up to and including 15 days, or even more. The release rate and the duration of the release of tilmicosin depends on several variables that can be manipulated to optimize the method for a particular application. Preferably the methods of the invention provide a pharmaceutically effective amount of tilmicosin to the horse or pig for at least 4-5 days after injection; and more preferably the tilmicosin is released in a pharmaceutically effective amount for 6 days, or even 7 days after injection. In other embodiments, it may also be desirable to manipulate variables so as to extend release time of tilmicosin even further than 15 days.

The methods of the invention therefore enable the administration of tilmicosin to animals that, if administered tilmicosin in presently available formulations, would result in toxicity to the treated mammal. Accordingly, it has not been possible to use tilmicosin in particular species due to safety considerations. In particular, the methods of the invention enable the administration of tilmicosin to horses and pigs. In one embodiment, the method of the invention involves administering tilmicosin to a horse. In one embodiment, the method of the invention involves administering tilmicosin to a pig. Without wishing to be bound by theory, it is believed that the controlled release of tilmicosin avoids or reduces the adverse effects often observed when tilmicosin is administered to horses or pigs using commercially available formulations. The methods of the invention, while avoiding or reducing adverse effects, however, provide a therapeutically effective amount of tilmicosin in the tissue of the horse or pig.

The lipophilic acid can be a saturated or unsaturated fatty acid of any specific number of carbons between 8 and 22, preferably a $C_8$-$C_{18}$ fatty acid, and more preferably a $C_{10}$-$C_{18}$ fatty acid. Representative $C_8$-$C_{22}$ fatty acids include, but are not limited to, caproic acid, lauric acid, myristic acid, palmitic acid, stearic acid, palmic acid, oleic acid, linoleic acid, and linolenic acid. Other lipophilic acids may also be used, for example dicarboxylic acids, such as sebacic acid; polymeric acids, such as lipophilic poly-carboxylic acids; and aromatic acids, such as benzoic acid. In preferred embodiments, the lipophilic acid is decanoic acid, lauric acid, oleic acid, linoleic acid, or myristic acid.

In another embodiment, the compositions used in the methods of the invention are a salt formed from tilmicosin and a polycarboxylic acid and the solvent is a pharmaceutically acceptable water soluble solvent, combined together under conditions to form an injectable composition that precipitates when injected into water at room temperature or precipitates in physiological ("in vivo") environments. By "polycarboxylic acid" is meant a molecule containing at least two carboxyl groups. In preferred embodiments the polycarboxylic acid is polyaspartic acid, polyacrylic acid, polysebacic acid, polybenzoic acid, or combinations thereof. By "poly" is meant two or more.

The pharmaceutically acceptable solvent can be an organic solvent. In preferred embodiments, the solvent is pyrrolidone, N-methylpyrrolidone, polyethylene glycol, propylene glycol, glycerol formal, isosorbid dimethyl ether, ethanol, dimethyl sulfoxide, tetrahydrofurfuryl alcohol, triacetin, or any combination of these, or another solvent found to have similar acceptable properties such as being non-toxic and soluble in water. In one embodiment, the pharmaceutically acceptable solvent is N-methyl pyrrolidone (NMP). In another embodiment, the pharmaceutically acceptable solvent is propylene glycol (e.g., at about 10%) in glycerol formal, with or without stabilizers.

In one embodiment, the lipophilic acid is lauric acid and the pharmaceutically acceptable solvent is propylene glycol, polyethylene glycol, glycerol formal, or an appropriate combination of these.

In various embodiments, the compositions used in the methods of the invention may further comprise a second pharmaceutically active compound. Representative classes of second pharmaceutically active compounds include, but are not limited to, other antibacterials, antifungals, antiparasitics, antivirals, and antiinflammatories.

The tilmicosin compositions used in the methods of the invention are a stable, injectable, formulation that precipitates when injected in the horse or pig to form a depot that slowly releases tilmicosin over an extended period of time. The compositions used in the methods of the invention precipitate and release the tilmicosin over time when introduced or injected into an aqueous environment. When injected into the horse or pig, at least a portion of the composition forms a drug depot that releases the tilmicosin over time.

The present invention therefore offers important advantages over previously available methods of administering tilmicosin. Without wishing to be bound by theory, it is believed that the methods of the present invention, by providing controlled release of tilmicosin, reduces the toxicity of tilmicosin when it is administered to horses and pigs. The methods of the invention also offer the advantage of being able to administer tilmicosin in an efficient manner, thereby requiring a smaller investment in time and resources, compared to using previous modes of administering tilmicosin.

The summary of the invention described above is not limiting and other features and advantages of the invention will be apparent from the following detailed description of the preferred embodiments, as well as from the claims.

DETAILED DESCRIPTION OF THE INVENTION

Figure 1:
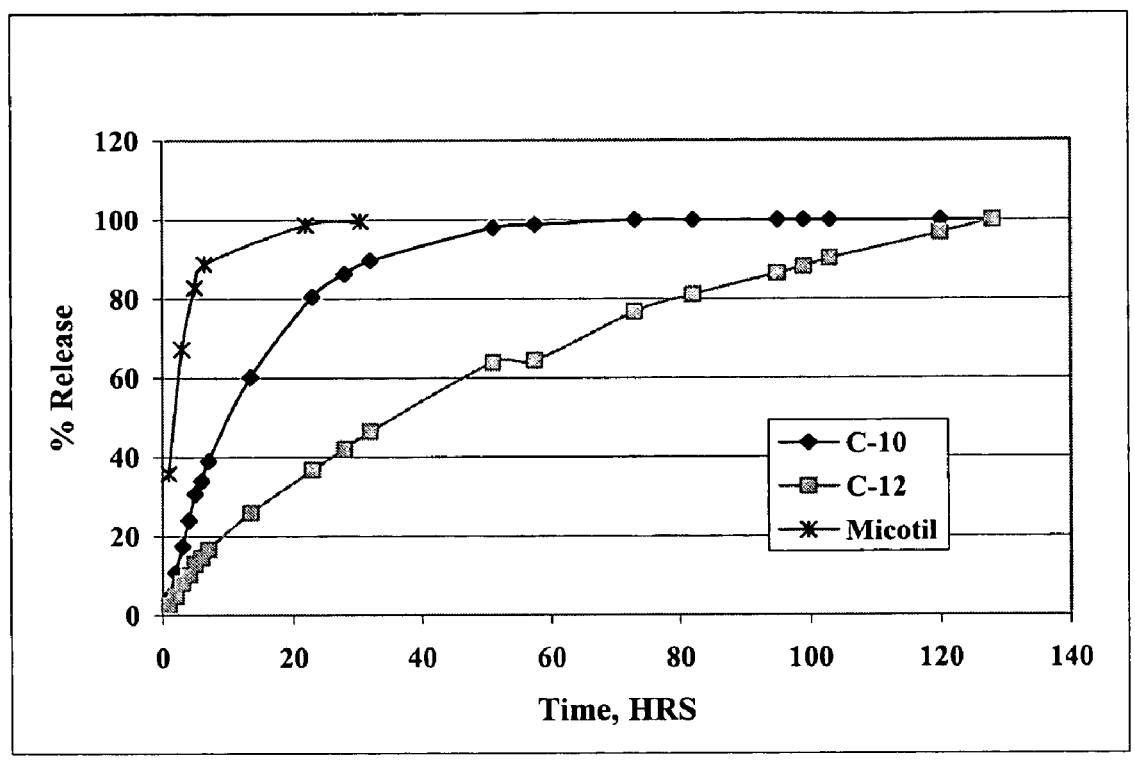
FIG. 1 is a graphical depiction illustrating that the rate of release of tilmicosin is affected by the chain length of the fatty acid selected. The solvent is N-methyl pyrrolidone and the lipophilic acid is (♦) decanoic acid and (■) lauric acid. Also provided is the rate of release of tilmicosin from (x) Micotil® (commercially available from Eli Lilly & Co., Indianapolis, Ind.).

The present invention provides methods of treating a bacterial infection in a horse or a pig. The method involves administering to the horse or pig a composition comprising (i) a salt made from tilmicosin and a lipophilic acid and (ii) a pharmaceutically acceptable solvent combined together to form an injectable composition that precipitates when injected into water.

The compositions used in the methods of the present invention can be prepared using a variety of lipophilic acids, saturated or unsaturated fatty acids, cholic acids, phosphatidic acids, dicarboxylic acids such as sebacic acid, or any acid that, when combined with tilmicosin, renders the resulting salt insoluble in water but soluble in a water soluble solvent. In one embodiment, the fatty acid has an octanol/water partition coefficient of 100 or more. In another embodiment, the octanol/water partition coefficient is 50 or more. In another embodiment, the octanol/water partition coefficient is 40 or more. In another embodiment, the octanol/water partition coefficient is 25 or more. In another embodiment, the octanol/water partition coefficient is 10 or more.

By "salt" is meant two compounds that are not covalently linked but are chemically bound through ionic attractions.

By "water miscible" is meant that the solvent is capable of mixing in any ratio in water without separation of two phases. By "water soluble" is meant that the solvent has some significant level of solubility in aqueous solutions, e.g., triacetin is considered a water soluble solvent since it is soluble in water at a ratio of about 1:14.

By a "lipophilic counterion" is meant an ionic form of a fat soluble molecule. The lipophilic counterion may preferably be the anion of a fatty acid, but may also be the anion of another fat soluble molecule. The counterion has at least one charge opposite to that of a chemical group on an opposing salt member, thereby causing an ionic attraction between the two molecules.

By "injectable formulation" or "injectable composition" is meant a formulation or composition that can be drawn into a syringe and injected subcutaneously, intraperitoneally, or intramuscularly into a horse or pig without causing adverse effects due to the presence of solid materials in the composition. Solid materials include, but are not limited to, crystals, gummy masses, and gels. Typically, a formulation or composition is considered to be injectable when no more than 10% of the formulation is retained on a 0.22 μm filter when the formulation is filtered through the filter at 98° F.

By "pharmacologically active compound" is meant a chemical compound that causes a pharmacological effect in the treated horse or pig. For example, the effect may be to destroy or prevent growth of bacteria, viruses, or parasites; reduce inflammation; or other pharmaceutical and measurable effect in the treated horse or pig.

By the verb "precipitate" is meant that the composition forms a precipitate, or solid, when injected into water or into a physiological (in vivo) environment. A precipitate is an insoluble solid formed in solution at room temperature in vitro or in a physiological (in vivo) environment. The precipitate can take many forms such as, for example, a solid, a crystal, a gummy mass, or a gel. A composition of the invention precipitates in water when at least 10% of the composition is retained on a 0.22 μm filter when the composition is mixed with water and filtered at 98° F.

By "pharmaceutically effective amount" is meant an amount that exerts a measurable and medically significant effect on the treated horse or pig, resulting in progress towards curing or preventing the subject disease, or alleviating or preventing the condition that was the reason for treatment. Typically, the condition is a bacterial infection.

A "pharmaceutically acceptable solvent" is a liquid that dissolves a salt of tilmicosin and a lipophilic counterion and that is suitable for use with horses or pigs without undue adverse side effects (such as toxicity, irritation, and allergic response) commensurate with a reasonable benefit/risk ratio.

The compositions used in the methods of the invention can contain high concentrations of tilmicosin. In one embodiment, tilmicosin is included in the composition in an amount ranging from about 10% to 60% (w/v). A person of ordinary skill in the art, however, will realize this range may be varied widely, depending on, for example, the lipophilic acid selected, the solvent selected, the injectability of the final product, and any other relevant needs of the particular application. In one embodiment, the compositions used in the methods of the invention include tilmicosin in an amount as low as about 10%, about 5%, or even about 1% and still provide a useful effect. Similarly, tilmicosin can be included in the compositions used in the methods of the invention in amounts of 70%, or even higher as needs require. No exotic excipients or carriers are required. The compositions are easily filtered, thereby simplifying the manufacturing process. It is also believed that the exclusion of water from the compositions imparts greater stability to the compositions, and inhibits the growth of microorganisms. The processes for preparing the compositions, as described herein, are simple, and administration according to the present invention typically results in milder reactions at the injection site due to the neutralization of the pharmacologically active compound.

The compositions of the invention can be injected at a dose ranging from about 1 mg tilmicosin/kg to about 100 mg tilmicosin/kg. In one embodiment, the compositions of the invention are injected at a dose ranging from about 1 mg tilmicosin/kg to about 75 mg tilmicosin/kg. In one embodiment, the compositions of the invention are injected at a dose ranging from about 5 mg tilmicosin/kg to about 50 mg tilmicosin/kg. In one embodiment, the compositions of the invention are injected at a dose ranging from about 10 mg tilmicosin/kg to about 40 mg tilmicosin/kg.

The methods of the present invention provides the ability to modulate the release rate and release time of tilmicosin so as to permit tilmicosin to be administered to mammals that, if administered tilmicosin using presently available formulations, would be toxic and could even cause death. For example, the release rate of tilmicosin can be modulated by varying the lipophilicity and molecular weight of the lipophilic counterion used to make the salt. For example, lauric acid salts of tilmicosin are usually released more slowly than decanoate salts. In addition, higher concentrations of the salt in the formulation usually yield slower release rates. The decanoate salt of tilmicosin is released more slowly from a 60% tilmicosin-fatty acid salt formulation that from a 30% tilmicosin-fatty acid salt formulation. Similarly, as explained herein, other variables such as lipophilic counterion, solvent, and salt concentration can be manipulated to lengthen or shorten the release time of tilmicosin to an acceptable rate.

The pharmaceutically acceptable solvent may be a water miscible or water soluble solvent, and preferably is a water miscible solvent. Mixtures of water soluble and/or water miscible solvents may also be utilized. The person of ordinary skill in the art will realize that various water soluble solvents may be mixed to optimize the composition for a particular application. For example, a mixture of polyethylene glycol, propylene glycol, and glycerol formal may be mixed in various ratios to provide an optimal solvent.

Tilmicosin, has two basic amine sites. Therefore, typically each equivalent of tilmicosin included in the compositions used in the methods of the invention forms a salt with two equivalents of lipophilic acid, if the lipophilic acid is a mono-protic acid, or with 1 equivalent of lipophilic acid, if the lipophilic acid is a diprotic acid. In other embodiments, however, the compositions used in the methods of the invention, i.e., compositions including a salt of tilmicosin with a lipophilic counterion, can further include the non-salt or free form of tilmicosin. Compositions further comprising the free form of tilmicosin provide an initial dose or "burst" of tilmicosin. Since tilmicosin, has two basic amine sites the compositions used in the methods of the invention will include free tilmicosin if there is less than 1 equivalent of mono-protic lipophilic acid or less than 2 equivalents of di-protic lipophilic acid per equivalent of tilmicosin.

Without wishing to be bound by any particular theory, it is believed that when the compositions used in the methods of the invention are injected into a horse or pig, the solvent diffuses away from the injection site as aqueous body fluids diffuse towards the injection site, resulting in the salt of tilmicosin and the lipophilic acid precipitating in the treated horse or pig. The precipitate may take many forms, for example, a solid, a crystal, a gummy mass, or a gel. The precipitate acts as a drug depot in the horse or pig that then releases tilmicosin over a period of time. Release times can be adjusted to provide a therapeutically effective amount of tilmicosin to the horse or pig for at least 3 days, at least 4 days, at least 5 days, at least 6 days at least 7 days, or any specific number of days up to and including at least 15 days, or even longer, as desired. By "drug depot" is meant a concentration or precipitation of tilmicosin within the body of the treated horse or pig that releases a pharmaceutically effective amount of tilmicosin over time.

The fatty acid chain length, the particular combinations of fatty acids, the percent of tilmicosin:lipophilic counterion salt in the composition, and the choice of the pharmaceutically acceptable solvent all influence the release rate of tilmicosin. Thus, the release rate of tilmicosin can be conveniently and easily managed by manipulating these and other variables. It was also found that the compositions were stable to autoclave sterilization.

In various embodiments, the compositions used in the methods of the invention may further comprise a second pharmaceutically active compound. Representative classes of second pharmaceutically active compounds include, but are not limited to, other antibacterials, antifungals, antiparasitics, antivirals, and antiinflammatories.

Representative second pharmaceutically active compounds that are antibacterials include, but are not limited to, β-lactam antibiotics such as penicillins, amoxicillin, ampicillin, and cephalosporins; macrolide antibiotics such as oleandomycin and erythromycin; tetracyclines such as tetracycline, oxytetracycline, and chlortetracycline; procaine penicillin G; quinolones such as nalidixic acid and norfloxacin; sulfonamides; chloramphenicol; florfenicol; thiamphenicol, aminoglycosides such as streptomycin, kanamycin, and gentamycins; nucleoside antibiotics such as polyoxin B; actinorhodine; bacitracin; candicidin A; ceftiofor; clindamycin; cycloheximide; cycloserine; fosfomycin; griseofulvin; metronidazole; monensin; novobiocin; rifampin; streptothricin; tetranactin; tilmicosin; tylosin; actinomycin D; adriamycin; bleomycin B2; glycolipids such as moenomycin A; mitomycin C; nojirimycin; valinomycin; and vancomycin; (See, e.g., Bradford P. Smith, *Large Animal Internal Medicine,* 2nd ed., Mosby, St. Louis, 1996, p. 644, and S. Birchard and R. Sherding, *Saunders Manual of Small Animal Practice*, W.B. Saunders Company, Philadelphia, 1994, p. 739).

Representative second pharmaceutically active compounds that are antifungals include, but are not limited to, amphotericin B, ketaconazole, miconazole, 5-fluorocytosine, enilconazole, itraconazole, thiabendazole, and iodides (See, e.g., Bradford P. Smith, *Large Animal Internal Medicine,* 2nd edn., Mosby, St. Louis, 1996, p. 576, and S. Birchard and R. Sherding, *Saunders Manual of Small Animal Practice*, W.B. Saunders Company, Philadelphia, 1994, p. 576).

Representative second pharmaceutically active compounds that are antivirals include, but are not limited to, interferon (See, e.g., Bradford P. Smith, *Large Animal Internal Medicine,* 2nd edn., Mosby, St. Louis, 1996, p. 646).

Representative second pharmaceutically active compounds that are antiparasitics include, but are not limited to, benzimidazoles, such as thiabendazole, fenbendazole, mebendazole, oxfendazole, oxibendazole, albendazole, parbendazole, and febantel; tetrahydropyridines such as morantel tartrate/pyrantel pamoate; levamisole, organophosphates such as haloxon, coumaphos, trichlorfon, and dichlorvos; piperazine salts; ivermectin; and phenothiazine (See, e.g., Bradford P. Smith, *Large Animal Internal Medicine,* 2nd edn., Mosby, St. Louis, 1996, p. 1688).

Representative second pharmaceutically active compounds that are antiinflammatories include, but are not limited to, steroids such as betamethazone; corticosteroids such as dexamethasone; antihistamines; and non-steroidal antiinflammatory drugs such as aspirin, flunixin meglumine, phenylbutazone, and ibuprofin (See, e.g., Bradford P. Smith, *Large Animal Internal Medicine,* 2nd edn., Mosby, St. Louis, 1996, p. 645).

If the second pharmaceutically active compound is a basic compound it can also be present in the form of a salt of a lipophilic acid or other acid.

In one embodiment, the methods of the invention are used to treat a bacterial infection of the respiratory tract.

In one embodiment, the methods of the invention are used to treat a bacterial infection caused by *spirochete Borrelia*, e.g., *Borrelia burgdorferi. Spirochete Borrelia* causes Lyme disease.

In another embodiment, the methods of the invention are used to treat a bacterial infection caused by *Staphylococcus aureus.*

In another embodiment, the methods of the invention are used to treat a bacterial infection caused by *Streptococcus pyogenes.*

In another embodiment, the methods of the invention are used to treat a bacterial infection caused by *Bordetella bronchiseptica. Bordetella bronchiseptica* is responsible for many respiratory infections. For example, in pigs, *Bordetella bronchiseptica* causes atrophic rhinitis and pneumonia.

In another emboiment, the compositions of the invention are useful for treating a respiratory disease associated with mycoplasma. For example, mycoplasma hypopneumoniae is an obligatory pathogen of the respiratory tracts of pigs. The organisms infects the airways of the respiratory system and is recognized as an initiator or potentiator of more serious respiratory diseases caused by other primary or opportunistic pathogens. By "associated with" mycoplasma means that the presence of mycoplasma is an initiator or potentiator of the disease.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

In Vitro Release of Tilmicosin—Effect of Lipophilic Acid

10 Grams (0.0115 moles) of tilmicosin and 0.0253 moles of either decanoic acid or lauric acid were weighed into a flask and made up to a final volume of 100 mL with N-methyl-pyrrolidone. The resulting solution was then stirred for 60 minutes to provide a clear solution. One mL aliquots of the resulting solutions were then sealed in dialysis bags, and the dialysis bag suspended in flasks containing 150 ml of phosphate-buffered saline at pH 7.4. A precipitate was observed to form in the dialysis bag within about 1 hour. Aliquots of saline were then removed at various intervals and the concentration of tilmicosin in the saline was determined using high pressure liquid chromatography (HPLC).

For HPLC analysis 100 µL of the saline solution was injected on a Phenomenex Luna 5 µM phenyl-hexyl 100A, 250×4.6 mm analytical column operated at a flow rate of 1.7 mL/min. The HPLC was interfaced to a UV detector operated at 285 nm. The HPLC column was eluted using gradient elution according to the following profile:

| Time | Percent Pump A | Percent Pump B |
|---|---|---|
| 0 | 30 | 70 |
| 10.5 | 85 | 15 | wherein the solvent in pump A was 25 mM phosphate buffer at pH 2.4 and the solvent in pump B was acetonitrile. The total run time was 25 min.

The release of tilmicosin as a function of time from the decanoic acid (C-10) and lauric acid (C-12) salts of tilmicosin are shown in FIG. 1. These results show that tilmicosin continued to diffuse out of the bag for more than 120 hours. The results also show that the longer the chain length of the acid, the slower tilmicosin is released. In contrast, Micotil® (commercially available from Eli Lilly of Indianapolis, Ind.), a phosphate salt of tilmicosin, is readily soluble and rapidly diffuses from the bag.

Example 2

In Vitro Release of Tilmicosin—Effect of Solvent

Figure 2:
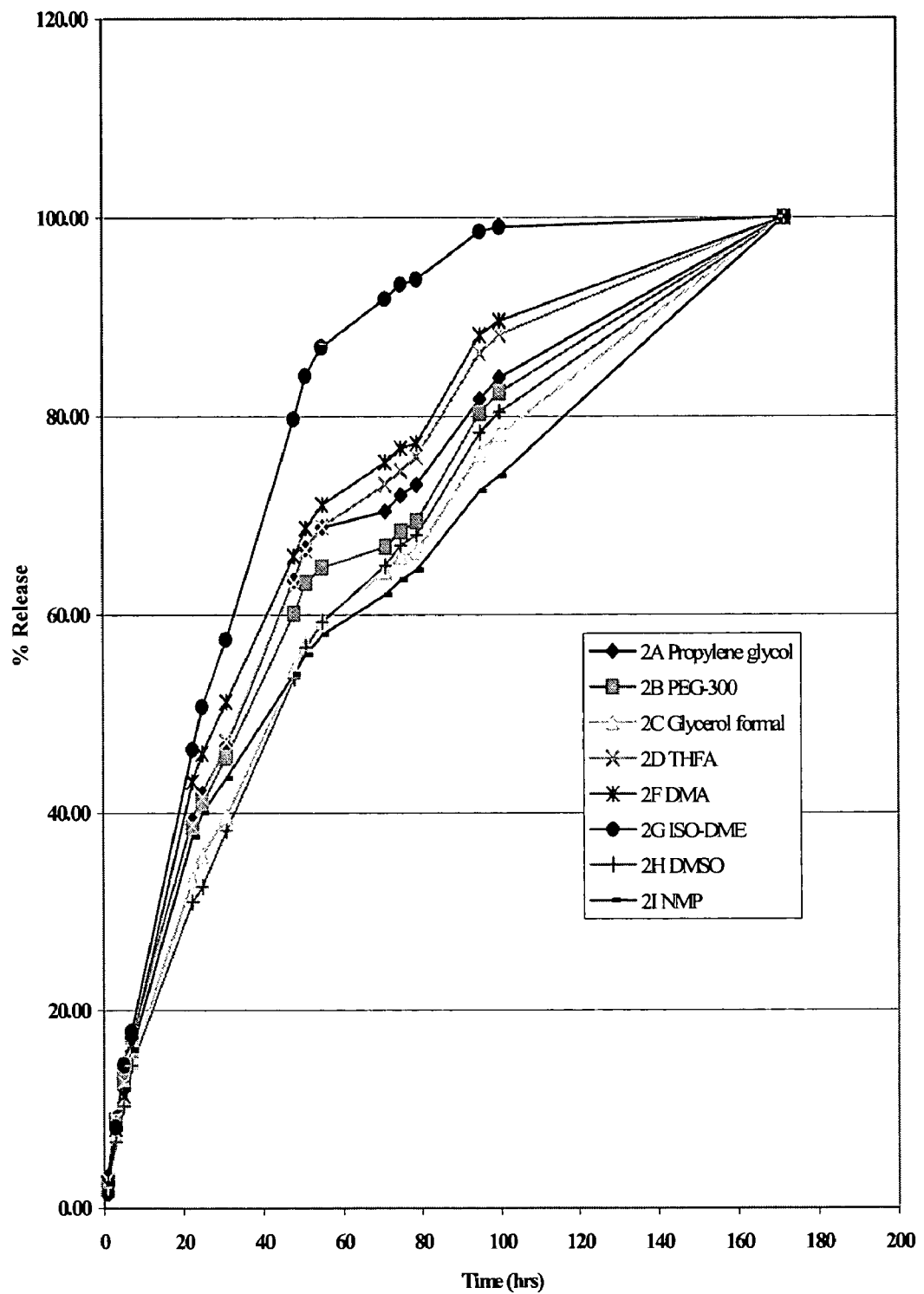
FIG. 2 is a graphical depiction illustrating the effect of solvent on the in vitro release rate of tilmicosin from a formulation of the di(decanoic) acid salt of tilmicosin in various solvents. The concentration of the di(decanoic) acid salt of tilmicosin in the formulation is 100 mg/mL. Abbreviations are as follows: PEG=polyethylene glycol, THFA=tetrahydrofurfuryl alcohol, DMA=dimethyl acetamide, ISO-DME=isosorbid dimethyl ether, DMSO=dimethyl sulfoxide, NMP=N-methyl pyrrolidone.

Solutions of the di(decanoic acid) salt of tilmicosin were prepared in several water-miscible solvents by combining 10 grams (0.0115 moles) of tilmicosin and 0.0253 moles of decanoic acid in 100 mL of various solvents. In vitro release rates were then measured using the dialysis method of Example 1. The rates of release of tilmicosin as a function of time are shown in FIG. 2. The results show that the rate of release of tilmicosin varies with the solvent, but that all of the solvents provide a slower release rate than that observed with the phosphate salt, i.e., Micotil® as shown in FIG. 1.

Example 3

In Vitro Release of Tilmicosin—Effect of Tilmicosin Concentration

Figure 3:
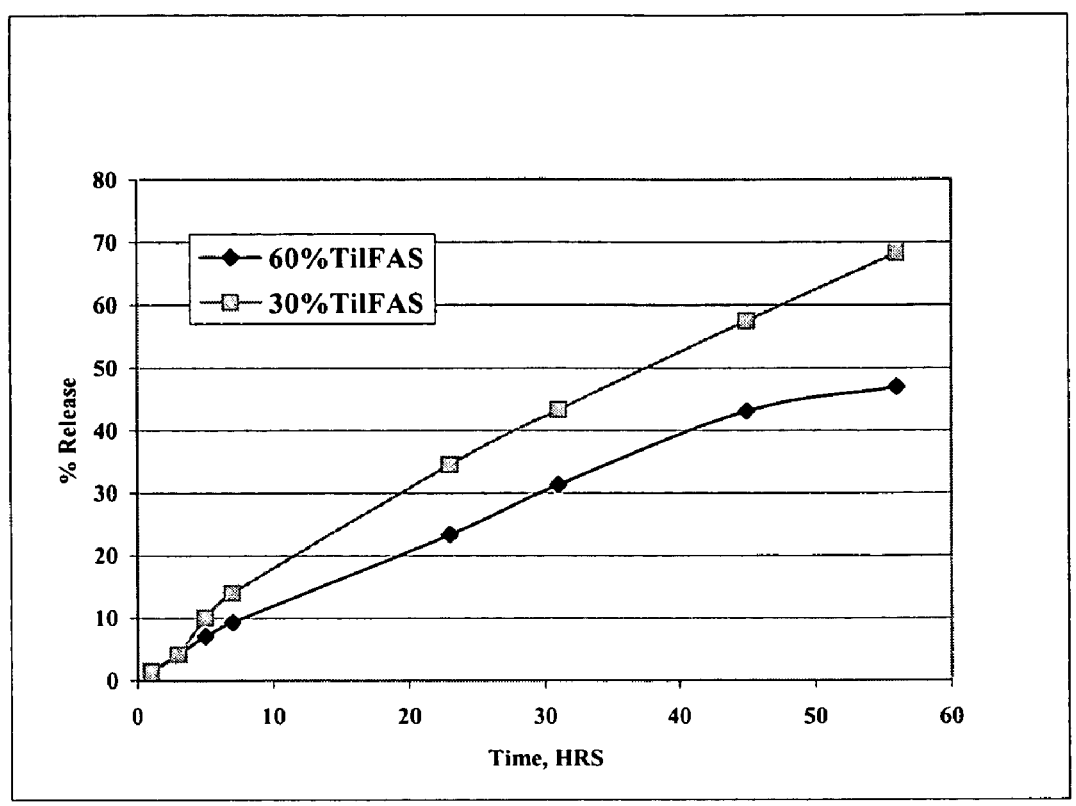
FIG. 3 is a graphical depiction illustrating that the release rate of tilmicosin is a function of the concentration of fatty acid salt. The lipophilic acid is decanoic acid and the solvent is N-methylpyrrolidone (NMP). (♦) 60% tilmicosin-di(decanoic) acid salt in NMP and (■) 30% tilmicosin-di(decanoic) acid salt in NMP.

Solutions of the di(decanoic acid) salt of tilmicosin were prepared by combining 30 grams (0.0345 moles) or 60 grams (0.0690 moles) of tilmicosin with 2 equivalents of decanoic acid in N-methyl-pyrrolidone and filling to a final volume of 100 ml. The in vitro release rates were measured using the dialysis method of Example 1. The data are presented in FIG. 3. The data demonstrate that higher concentrations of tilmicosin result in a slower release rate of tilmicosin.

Example 4

Tilmicosin Decanoic Acid Salt Formulation

To a mixture of 256 g of propylene glycol and 1403 g of stabilized glycerol formal in a 4 L stainless steel container equipped with over-head stirrer and a heating jacket at 40° C., was added 332 g of lauric acid with stirring. Stirring was continued to provide a clear solution. Tilmicosin (686 g, 91.1% pure) was then slowly added with stirring while maintaining the mixture at a temperature below 40° C. After all the tilmicosin was added, the resulting mixture was stirred to provide a clear solution. To the resulting solution was added sufficient glycerol formal to provide a final solution weight of 2855.5 g to provide 2.5 liters of a solution of the di(decanoic acid) salt of tilmicosin. The final solution had a density of 1.142 g/mL.

Example 5

Tilmicosin Lauric Acid Salt Formulation

To a mixture of 259 g of propylene glycol and 1495 g of stabilized glycerol formal in a 4 L stainless steel container equipped with over-head stirrer and a heating jacket at 40° C., was added 260 g of melted lauric acid with stirring. Stirring was continued to provide a clear solution. Tilmicosin (686 g, 91.1% pure) was then slowly added with stirring while maintaining the mixture at a temperature below 40° C. After all the tilmicosin was added, the resulting mixture was stirred to provide a clear solution. To the resulting solution was added sufficient glycerol formal to provide a final solution weight of 2832.5 g to provide 2.5 liters of a solution of the di(lauric acid) salt of tilmicosin. The final solution had a density of 1.133 g/mL.

Example 6

Administration of Tilmicosin to Horses

Three foals (foal 1 (a 250 lb filly with black/white face and socks), foal 2 (a 500 lb chestnut filly), and foal 3 (a 470 lb sorrel colt)) were acclimated to feed and environment for 1 week and dewormed with ivermectin. On day 1 each foal received a 30 mg/kg dose of tilmicosin as a formulation of the di(decanoic acid) salt of tilmicosin in 10% propylene glycol in glycerol formal having a tilmicosin concentration of 250 mg/mL (i.e., foal 1 was administered 14 mL of the formulation, foal 2 was administered 27 mL of the formulation, and foal 3 was administered 26 mL of the formulation). The di(decanoic acid) salt of tilmicosin in 10% propylene glycol in glycerol formal having a tilmicosin concentration of 250 mg/mL was prepared as described in Example 4. The dose was administered as several intramuscular injections in the left hip using an 18 gauge 1½ inch needle with a 12 mL screw on syringe. Injection sites were clipped and cleaned prior to injection and the volume of each individual injection was 5 mL or less.

On day 2, all foals showed soreness in the left hip during the morning and evening but had good appetites and did not have diarrhea.

On day 3, all foals still showed soreness in the left hip.

On day 4, all foals were normal and continued to act normally through day 18.

Blood samples were withdrawn from foal 1 daily for 9 days following administration of the 30 mg/kg dose of the formulation of the di(decanoic acid) salt of tilmicosin in 10% propylene glycol in glycerol formal having a tilmicosin concentration of 250 mg/mL. Blood samples were analyzed for tilmicosin according to the following procedure:

(i) A Strata X-C 33 μm Cation Mixed-Mode Polymer 30 mg/mL cartridge was condition by washing with 1 mL of methanol and 1 mL of deionized water using gravity flow;

(ii) 1 mL of serum acidified with 20 μl of phosphoric acid was applied to the conditioned cartridge;

(iii) The column was washed with 1 mL of 0.1% $H_3PO_4$/$H_2O$, 1 mL of acetonitrile, and 2 mL of methanol;

(iv) The column was eluted with 4 mL ammonia in methanol (15% of 2M $NH_4OH$ in methanol);

(v) The solvent was removed from the eluant using a stream of nitrogen gas; and (vi) The resulting residue was then reconstituted with 1 mL of 50:50 methanol/50 mM phosphate buffer at pH 2.3 and the resulting solution analyzed by HPLC.

For HPLC analysis 100 μL was injected on a Phenomenex Luna 5 μM phenyl-hexyl 100A, 250×4.6 mm analytical column operated at a flow rate of 1.7 mL/min. The HPLC was interfaced to a UV detector operated at 285 nm. The HPLC column was eluted using gradient elution according to the following profile:

| Time | Percent Pump A | Percent Pump B |
|------|----------------|----------------|
| 0    | 30             | 70             |
| 10.5 | 85             | 15             | wherein the solvent in pump A was 25 mM phosphate buffer at pH 2.4 and the solvent in pump B was acetonitrile. The total run time was 25 min. The serum concentration of tilmicosin was then determined by comparing the area under the curve for the HPLC peak corresponding to tilmicosin to a standard curve of peak areas v. known concentrations of tilmicosin in serum. The standard curve was prepared using the following concentrations of tilmicosin in serum 4, 2, 1, 0.5, and 0 μg/mL.

Figure 4:
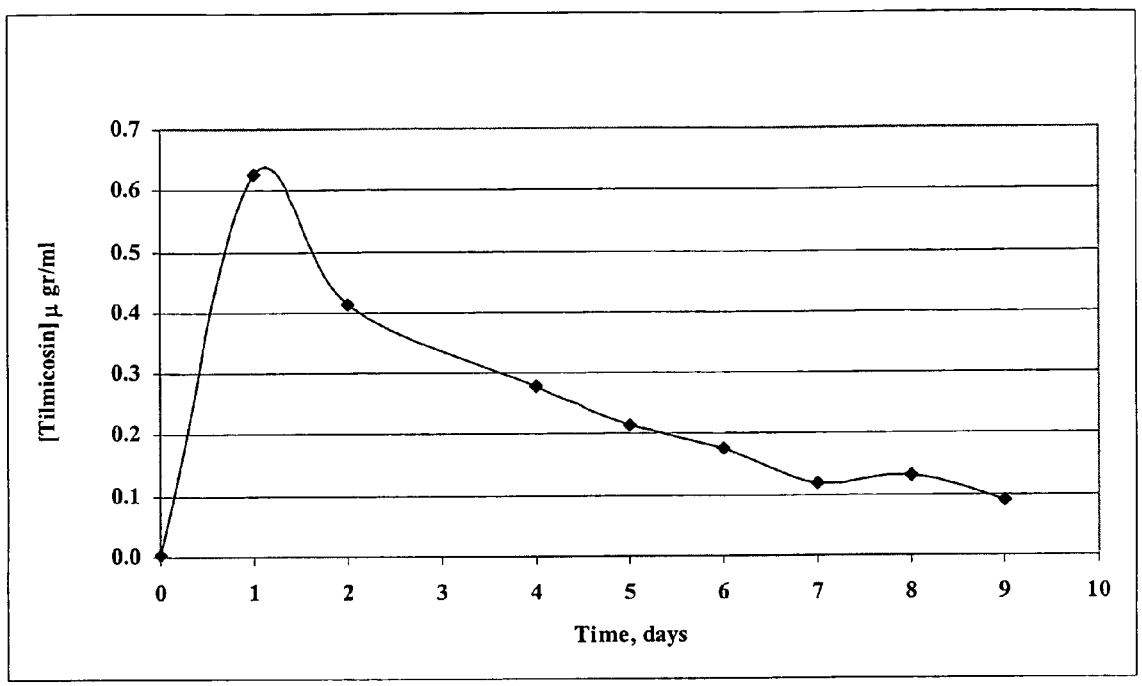
FIG. 4 is a graphical depiction of the serum concentration of tilmicosin as a function of time when tilmicosin is administered to a 250 lb. foal as a 30 mg/kg dose of a formulation of the di(decanoic) acid salt of tilmicosin in 10% propylene glycol in glycerol formal having a tilmicosin concentration of 250 mg/mL, i.e., 14 mL of the formulation is administered to the foal.

The serum concentration of tilmicosin as a function of time is provided in FIG. 4. These results show that a therapeutically effective concentration of tilmicosin is present in the horses blood for up to 9 days without having an adverse effect on the horse.

On day 19, each foal received a second 50 mg/kg dose of tilmicosin as a formulation of the di(decanoic acid) salt of tilmicosin in 10% propylene glycol in glycerol formal having a tilmicosin concentration of 250 mg/mL (i.e., foal 1 was administered 23 mL of the formulation, foal 2 was administered 45 mL of the formulation, and foal 3 was administered 43 mL of the formulation). The dose was administered as several intramuscular injections in the right hip in the same manner as the initial doses of tilmicosin were administered.

On day 20, each foal showed soreness in the right hip and a lame right rear with swollen semimembranosis/tendinosis. Each foal ate only about ½ of their feed. None of the foals had diarrhea.

On day 21, one of the foals was walking without problems and two of the foals still showed signs of soreness in the right hip.

On day 22, each foal still exhibited swelling through the hock but all were walking better.

On day 24 each foal appeared normal.

On day 29, each foal was euthanized. Post mortem analysis identified no gross lesions on any of the foals except for the site of injection. The 10 day old injection sites (right hip) were hemorrhagic in appearance. The 29 day old injection sites (left hip) were condensed, firm, yellowish areas of about 2-3 cm in diameter. Visual examination of the lung, liver, kidney, spleen, and heart showed no deformities with each organ appearing normal.

These results show that tilmicosin can be administered to horses at doses as high as 50 mg/kg using the compositions of the invention without being toxic. In contrast, administering tilmicosin using the commercially available formulation (Micotil®, commercially available from Eli Lilly & Co. of Indianapolis, Ind.) at dose of 10 mg/kg is typically fatal to horses.

Example 7

Administration of Tilmicosin to Pigs

Three pigs were administered a 100 mg/kg dose of the formulation of di(decanoic acid) salt of tilmicosin of Example 4. Another 3 pigs were administered a 100 mg/kg dose of the formulation of the di(lauric acid) salt of tilmicosin of Example 5. No adverse effects were observed in any of the six pigs. Blood samples were collected from each pig hourly for 8 h after administration of tilmicosin. Blood samples were analyzed for tilmicosin according to the following procedure:

(i) A C-18 cartridge was connected to a 20 mL syringe and to a MasterFlex L/S cartridge pump and conditioned with 10 mL of methanol followed by 10 mL of deionized water at a flow rate of less than 5 mL/min;

(ii) 1 mL of serum was then placed in the 20 mL syringe and eluted through the cartridge. The cartridge was then washed with 10 mL of 25% acetonitrile water followed by 10 mL of water;

(iii) The cartridge was then dried in a desiccator for 10 min under high vacuum;

(iv) The cartridge was eluted into a 2 mL volumetric flask to volume with 5% acetic acid in methanol and the resulting solution was stored at refrigerator temperature for about 12 h;

(v) After being at refrigerator temperature for about 12 h the sample was stirred using a vortex mixer and filtered into an amber HPLC vial using a pall acrodisk syringe filter; and (vi) The resulting solution analyzed by HPLC.

For HPLC analysis 100 μL was injected on to a Phenomenex Sphericlone 5 μM phenyl 25 cm×4.6 mm analytical column operated at a flow rate of 1.5 mL/min and equipped with a Phenomenex Phenyl(phenylpropyl) guard column. The HPLC was interfaced to a UV detector operated at 280 nm. The HPLC column was eluted using gradient elution according to the following profile:

| Time | Percent Pump A | Percent Pump B | Percent Pump C |
|---|---|---|---|
| 0.0 | 50 | 50 | 0 |
| 3.0 | 50 | 50 | 0 |
| 4.0 | 15 | 85 | 0 |
| 5.0 | 15 | 0 | 85 |
| 25.0 | 25 | 0 | 75 |
| 25.1 | 50 | 50 | 0 |
| 40.0 | 50 | 50 | 0 | wherein the solvent in pump A was 50:50 acetonitrile:water, the solvent in pump B was 15:85 acetonitrile:water, and the solvent in pump C was 20 mM dibutylamine trifluoroacetic acid (prepared by adding 3.40 mL of dibutylamine to 700 mL of deionized water, slowly adding 1.54 mL of trifluoroacetic acid, and filling to a volume of 1 L with deionized water). The total run time was 40 min. The serum concentration of tilmicosin was then determined by comparing the area under the curve for the HPLC peak corresponding to tilmicosin to the area under the curve of a standard. The standard was tilmicosin dissolved in serum at a concentration of 1 µg/mL and treated in the same manner as described above.

Figure 6:
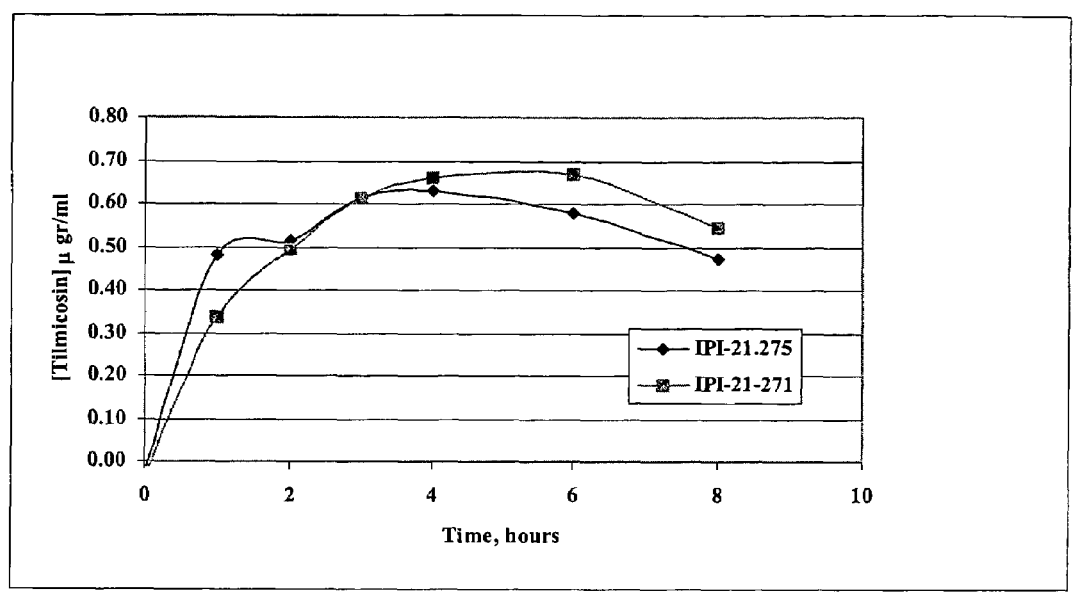
FIG. 6 is a graphical depiction of the average serum concentration of tilmicosin as a function of time when tilmicosin is administered to pigs (■) at a 100 mg/kg dose of the formulation of the di(decanoic acid) salt of tilmicosin of Example 4 and as (♦) a 100 mg/kg dose of the formulation of the di(lauric acid) salt of tilmicosin of Example 5. Each time point represents the average tilmicosin concentration for three pigs.

FIG. 6 shows the average serum concentration of tilmicosin as a function of time when tilmicosin is administered to pigs as (■) a 100 mg/kg dose of the formulation of the di(decanoic acid) salt of tilmicosin of Example 4 and as (♦) a 100 mg/kg dose of the formulation of the di(lauric acid) salt of tilmicosin of Example 5. Each time point represents the average tilmicosin concentration for three pigs.

Three pigs were then administered a 30 mg/kg dose of commercially available tilmicosin (Micotil®, commercially available from Eli Lilly & Co., Indianapolis, Ind.). Blood samples were withdrawn as a function of time and analyzed for tilmicosin using the HPLC method described above. One of the pigs (pig 1) died 3 h after the injection, one pig (pig 2) exhibited serious cardiac events after the injection before recovering, and one pig (pig 3) exhibited minor adverse clinical signs before recovering.

Figure 5:
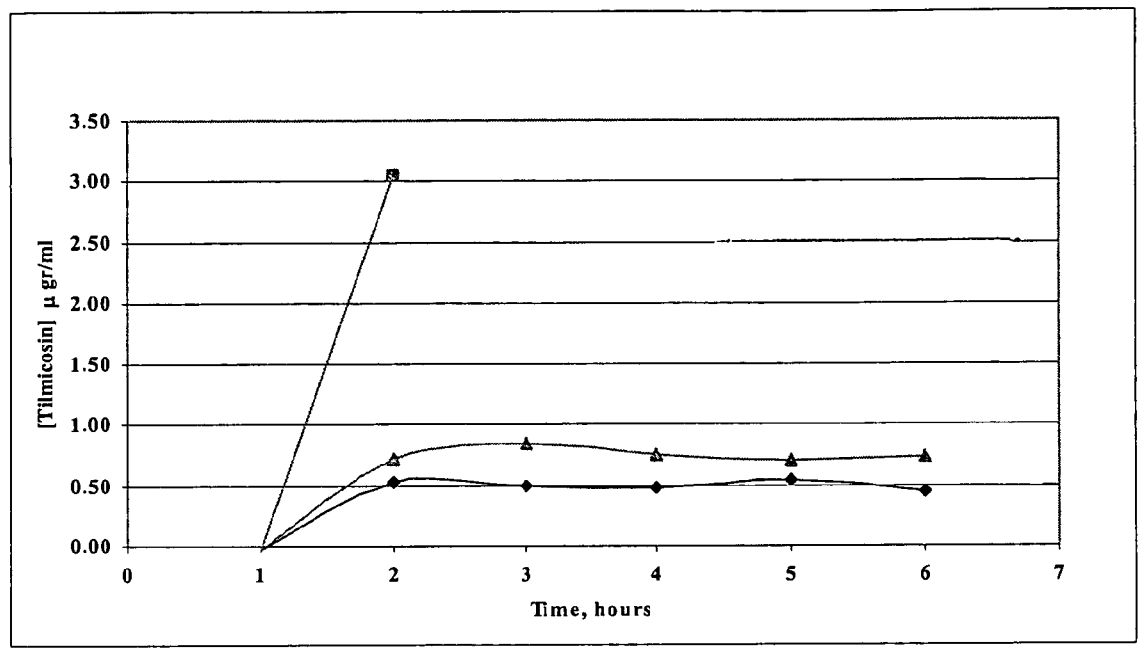
FIG. 5 is a graphical depiction of the serum concentration for tilmicosin as a function of time when tilmicosin is administered to each of three pigs at a dose of 30 mg/kg using commercially available tilmicosin (Micotil®, commercially available from Eli Lilly & Co. of Indianapolis, Ind.). (■) represents the data for pig 1, (▲) represents the data for pig 2, and (♦) represents the data for pig 3.

FIG. 5 shows the serum concentration of tilmicosin as a function of time when tilmicosin was administered to a pig at a dose of 30 mg/kg using commercially available tilmicosin (Micotil®, commercially available from Eli Lilly & Co. of Indianapolis, Ind.). (■) represents the data for pig 1, (▲) represents the data for pig 2, and (♦) represents the data for pig 3.

These results show that tilmicosin can be administered to pigs more safely using the compositions of the invention than using the commercially available formulation (Micotil®, commercially available from Eli Lilly & Co. of Indianapolis, Ind.) while still maintaining a similar serum concentration of tilmicosin.

In another experiment, three pigs were administered 45 mg/kg of the di(decanoic acid) salt of tilmicosin of Example 4, three pigs were administered 75 mg/kg of the di(decanoic acid) salt of tilmicosin of Example 4, three pigs were administered 45 mg/kg of the di(lauric acid) salt of tilmicosin of Example 5, three pigs were administered 75 mg/kg of the di(lauric acid) salt of tilmicosin of Example 5. There were no observable adverse reactions in any of the pigs. Also 3 pigs were administered 15 mg/kg using commercially available tilmicosin (Micotil®, commercially available from Eli Lilly & Co. of Indianapolis, Ind.). After 2 days the pigs were euthanized, the lungs harvested and frozen, and the tilmicosin concentration in lung tissues determined by the following procedure:

(i) Thaw tissue to room temperature and, after thawing, mince the tissue;

(ii) Accurately weigh about 5 g of minced lung tissue into a 50 mL centrifuge tube and add about 10 mL of methanol to the centrifuge tube;

(iii) Homogenize the tissue sample for about 5 min using an IKA homogenizer (commercially available from Cole-Parmer Instrument Company of Vernon Hills, Ill.);

(iv) Place the homogenized tissue sample in an ice bath and sonicate the sample twice for 30 sec with a 2 min between interval separating each sonicating step using a high intensity ultrasonic processor (commercially available from Cole-Parmer Instrument Company of Vernon Hills, Ill.) set at an amplitude of 70%;

(v) Centrifuge the tissue sample for 30 min at 10,000 rpm at 4° C. and decant the liquid layer into a 50 mL centrifuge tube to provide a first liquid layer;

(vi) Resuspend the tissue sample in a mixture of 10 mL of MeOH and 5 mL of 100 mM phosphate buffer, mix the tissue sample well, centrifuge the tissue sample for 30 min at 10,000 rpm at 4° C. to provide a second liquid layer, and combine the second liquid layer with the first liquid layer by decanting the second liquid layer into the centrifuge tube containing the first liquid layer;

(vii) Centrifuge the combined liquid layers for 10 min at 5,000 rpm, decant the resulting liquid layer into an erlenmeyer flask containing 70 mL of deionized water, and mix well to provide an analysis solution;

(viii) Connect a C-18 cartridge to a 20 mL syringe and to a MasterFlex L/S cartridge pump and condition the cartridge with 10 mL of methanol followed by 10 mL of deionized water at a flow rate of less than 5 mL/min;

(ix) Place the analysis solution into the 20 mL syringe and elute through the cartridge. Continue adding the analysis solution to the syringe and elute through the cartridge until all of the analysis solution is eluted through the cartridge. After all the analysis solution has been eluted through the cartridge, wash the cartridge with 10 mL of 25% acetonitrile water followed by 10 mL of deionized water;

(x) Dry the cartridge in a desiccator for 10 min under high vacuum;

(xi) Elute the cartridge into a 2 mL volumetric flask to volume with 5% acetic acid in methanol and store the resulting solution at refrigerator temperature for about 12 h;

(xii) After storing at refrigerator temperature for about 12 h, stir the solution using a vortex mixer and filter into an amber HPLC vial using a pall acrodisk syringe filter; and (xiii) Analyze the resulting solution for tilmicosin using the HPLC method described above.

The above analysis showed that tilmicosin, when administered using the compositions of the invention at a dose of 45 mg/kg or 75 mg/kg, was present in the lung tissue of the pigs at a concentration ranging from about 6.75 to 20.5 µg/g of lung tissue. In contrast, when tilmicosin was administered at a dose of 30 mg/kg using commercially available tilmicosin (Micotil®, commercially available from Eli Lilly & Co. of Indianapolis, Ind.), the concentration of tilmicosin in the lungs was only about 1.4 µg/g of lung tissue (average of three pigs). These results indicate that the compositions of the invention can be used to treat bacterial infections in the lungs of pigs i.e., provide a therapeutically effective amount of tilmicosin to the lung tissue of the pigs. Moreover, when the 45 mg/kg or 75 mg/kg dose was administered to pigs using the composition of the invention, the pigs showed no adverse effects. Indeed, as the above results show, tilmicosin can be administered to pigs at a dose of 100 mg/kg using the compositions of the invention without the pigs showing adverse effects. In contrast, administering the 30 mg/kg of tilmicosin using a commercially available formulation (Micotil®, commercially available from Eli Lilly & Co. of Indianapolis, Ind.) results in serious adverse effects for the pigs. Other studies also show similar toxicity when Micotil® is administered to pigs (See, W. H. Jordan, et al., A Review of the Toxicology of the Antibiotic MICOTIL 300, Vet. Hum. Toxicol. 35(2), 151-157 April 1993).

While the invention has been described and exemplified in sufficient detail for those skilled in this art to make and use it, various alternatives, modifications, and improvements should be apparent without departing from the spirit and scope of the invention.

One skilled in the art will readily appreciate that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims. It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A method of treating a bacterial infection in a horse or a pig comprising administering to the horse or pig by injection a composition comprising (i) a salt made from tilmicosin and a lipophilic acid and (ii) a pharmaceutically acceptable solvent wherein the composition is injectable and precipitates when injected into water.

2. The method of claim 1, wherein the composition is administered to a horse.

3. The method of claim 1, wherein the composition is administered to a pig.

4. The method of claim 1, wherein the lipophilic acid is a $C_8$-$C_{22}$ fatty acid, a dicarboxylic acid, a polycarboxylic acid, or an aromatic acid.

5. The method of claim 4, wherein the lipophilic acid is a $C_8$-$C_{22}$ fatty acid.

6. The method of claim 5, wherein the lipophilic acid is a $C_8$-$C_{18}$ fatty acid.

7. The method of claim 6, wherein the lipophilic acid is a $C_{10}$-$C_{18}$ fatty acid.

8. The method of claim 5, wherein the $C_8$-$C_{22}$ fatty acid is decanoic acid, lauric acid, oleic acid, linoleic acid, or myristic acid.

9. The method of claim 4, wherein the lipophilic acid is a dicarboxylic acid.

10. The method of claim 9, wherein the dicarboxylic acid is sebacic acid.

11. The method of claim 4, wherein the lipophilic acid is a polycarboxylic acid.

12. The method of claim 11, wherein the polycarboxylic acid is polyaspartic acid, polyacrylic acid, polysebacic acid, or polybenzoic acid.

13. The method of claim 1, wherein the pharmaceutically acceptable solvent is pyrrolidone, N-methyl pyrrolidone, polyethylene glycol, propylene glycol, glycerol formal, isosorbid dimethyl ether, ethanol, dimethyl sulfoxide, tetrahydrofurfuryl alcohol, triacetin, or a combination thereof.

14. The method of claim 13, wherein the pharmaceutically acceptable solvent is N-methyl pyrrolidone.

15. The method of claim 13, wherein the solvent is a mixture of propylene glycol and glycerol formal.

16. The method of claim 15, wherein the solvent is 10 percent by volume propylene glycol in glycerol formal.

17. The method of claim 1 wherein, the lipophilic acid is lauric acid or decanoic acid and the pharmaceutically acceptable solvent is propylene glycol, polyethylene glycol, glycerol formal, or a combination thereof.

18. The method of claim 1, wherein the lipophilic acid is lauric acid or decanoic acid, the pharmaceutically acceptable solvent is 10 percent by volume propylene glycol in glycerol formal, and the tilmicosin is present at a concentration of about 250 mg/mL.

19. The method of claim 1, wherein the amount of tilmicosin in the composition ranges from about 10 to 60 percent (w/v) of the composition.

20. The method of claim 1, wherein the amount of tilmicosin in the composition is less than about 10 percent (w/v) of the composition.

21. The method of claim 20, wherein the amount of tilmicosin in the composition ranges from about 1 to 10 percent (w/v) of the composition.

22. The method of claim 1, wherein the amount of tilmicosin in the composition is greater than about 60 percent (w/v) of the composition.

23. The method of claim 1, wherein the composition provides a pharmaceutically effective amount of tilmicosin in the blood of the horse or pig for at least 3 days.

24. The method of claim 23, wherein the composition provides a pharmaceutically effective amount of tilmicosin to the horse or pig for at least 5 days.

25. The method of claim 24, wherein the composition provides a pharmaceutically effective amount of tilmicosin to the horse or pig for at least 7 days.

* * * * *